United States Patent
Yamamoto et al.

(10) Patent No.: US 11,225,643 B2
(45) Date of Patent: Jan. 18, 2022

(54) METHOD FOR PRODUCING ENDOTHELIAL CELLS

(71) Applicant: TAKARA BIO INC., Kusatsu (JP)

(72) Inventors: Yuki Yamamoto, Kusatsu (JP); Tatsuji Enoki, Kusatsu (JP); Yasuhiro Tosaka, Kusatsu (JP); Yoko Yamaguchi, Kusatsu (JP); Junichi Mineno, Kusatsu (JP)

(73) Assignee: TAKARA BIO INC., Kusatsu (JP)

( * ) Notice: Subject to any disclaimer, the term of this patent is extended or adjusted under 35 U.S.C. 154(b) by 0 days.

(21) Appl. No.: 16/465,920

(22) PCT Filed: Dec. 1, 2017

(86) PCT No.: PCT/JP2017/043316
§ 371 (c)(1),
(2) Date: May 31, 2019

(87) PCT Pub. No.: WO2018/101466
PCT Pub. Date: Jun. 7, 2018

(65) Prior Publication Data
US 2020/0071675 A1 Mar. 5, 2020

(51) Int. Cl.
*C12N 5/071* (2010.01)
*A01N 1/02* (2006.01)

(52) U.S. Cl.
CPC ......... *C12N 5/0692* (2013.01); *A01N 1/0284* (2013.01); *C12N 2501/115* (2013.01); *C12N 2501/155* (2013.01); *C12N 2501/16* (2013.01); *C12N 2501/165* (2013.01); *C12N 2501/999* (2013.01); *C12N 2502/1329* (2013.01); *C12N 2506/02* (2013.01); *C12N 2506/45* (2013.01)

(58) Field of Classification Search
CPC ............ C12N 5/0692; C12N 2501/115; C12N 2501/155; C12N 2501/16; C12N 2501/165; C12N 2501/999; C12N 2502/1329; C12N 2506/02; C12N 2506/45; A01N 1/0284
See application file for complete search history.

(56) References Cited

U.S. PATENT DOCUMENTS

| | | |
|---|---|---|
| 2012/0021519 A1 | 1/2012 | Ichida et al. |
| 2014/0056859 A1 | 2/2014 | Okano et al. |
| 2015/0147299 A1 | 5/2015 | Rafii et al. |
| 2015/0329821 A1 | 11/2015 | Ang |
| 2016/0038544 A1 | 2/2016 | Keller et al. |
| 2016/0145581 A1 | 5/2016 | Deng et al. |
| 2016/0215263 A1 | 7/2016 | Keller et al. |
| 2016/0244719 A1 | 8/2016 | Thomson et al. |
| 2016/0312190 A1 | 10/2016 | Ghaedi et al. |
| 2018/0010092 A1 | 1/2018 | Dai et al. |
| 2018/0237745 A1 | 8/2018 | Pei et al. |

FOREIGN PATENT DOCUMENTS

| | | |
|---|---|---|
| CN | 105916978 A | 8/2016 |
| CN | 106434535 A | 2/2017 |
| JP | 2006-217801 A | 8/2006 |
| JP | 2015-519066 A | 7/2015 |
| JP | 2016-515825 A | 6/2016 |
| JP | 2016-528888 A | 9/2016 |
| JP | 2016-534738 A | 11/2016 |
| WO | WO 2011/090684 A2 | 7/2011 |
| WO | WO 2012/133945 A1 | 10/2012 |
| WO | WO 2014/192925 A1 | 12/2014 |
| WO | WO 2016/117510 A1 | 7/2016 |
| WO | WO 2016/134313 A1 | 8/2016 |
| WO | WO 2016/141084 A1 | 9/2016 |

OTHER PUBLICATIONS

Yoder et al, Curr Opin Hematol. May 2015; 22(3): 252-257.*
Palpant et al., Nature Protocols, 12(1): 15-31, including Supplemental Figures and Methods, published online Dec. 1, 2016.*
James et al., Nat Biotechnol. Feb. 2010 ; 28(2): 161-166.*
Ichida et al., Cell Stem Cell. Nov. 6, 2009; 5(5): 491-503.*
Bao et al., Stem Cell Res. Jul. 2015 ; 15(1): 122-129.*
Extended European Search Report for European Application No. 17875145.9, dated May 28, 2020.
Vogt et al., "The Specificities of Small Molecule Inhibitors of the TGFβ and BMP pathways," Cellular Signalling, vol. 23, 2011 (published online Jun. 29, 2011), pp. 1831-1842.
Drowley et al., "Human Induced Pluripotent Stem Cell-Derived Cardiac Progenitor Cells in Phenotypic Screening: A Transforming Growth Factor-β Type 1 Receptor Kinase Inhibitor Induces Efficient Cardiac Differentiation", Stem Cells Translational Medicine, vol. 5, 2016, pp. 164-174 (11 pages).
Partial Chinese Office Action and Search Report, dated Oct. 30, 2019, for Chinese Application No. 201780074594.2, with an English translation of the Office Action.
Xu et al., "Phenotypic correction of murine hemophilia A using an iPS cell-based therapy", PNAS, vol. 106, No. 3, Jan. 20, 2000, pp. 808-813(6 pages).
Decision of Grant issued in Japanese Patent Application No. 2018-521680, dated Sep. 27, 2018.

(Continued)

*Primary Examiner* — Thaian N. Ton
(74) *Attorney, Agent, or Firm* — Birch, Stewart, Kolasch & Birch, LLP

(57) ABSTRACT

The present invention relates to a method for producing endothelial cells, including carrying out: (a) inducing a population of mesoderm-lineage cells containing endothelial progenitor cells from pluripotent stem cells without forming an embryoid body; and (b) culturing the population of mesoderm-lineage cells containing endothelial progenitor cells in the presence of RepSox, in this order. According to the present invention, endothelial cells with high quality can be efficiently produced from pluripotent stem cells. The endothelial cells obtained by the method of the present invention are useful for the production of, for example, a myocardial sheet, and expected to be utilized in the treatment of a heart disease. A myocardial sheet can be produced by mixing the endothelial cells obtained by the method of the present invention with myocardial cells and mural cells and culturing the cells.

20 Claims, No Drawings

(56) References Cited

OTHER PUBLICATIONS

International Search Report (PCT/ISA/210) issued in PCT/JP2017/043316, dated Feb. 27, 2018.
James et al., "Expansion and maintenance of human embryonic stem cell-derived endothelial cells by TGFβ inhibition is Id1 dependent," Nature Biotechnology, vol. 28, No. 2, Jan. 17, 2010, pp. 161-166.
Notice of Grounds for Rejection issued in Japanese Patent Application No. 2018-521680, dated Jun. 19, 2018.
Written Opinion of the International Searching Authority (PCT/ISA/237) issued in PCT/JP2017/043316, dated Feb. 27, 2018.

* cited by examiner

METHOD FOR PRODUCING ENDOTHELIAL CELLS

TECHNICAL FIELD

The present invention relates to a method for producing endothelial cells with high quality from pluripotent stem cells.

BACKGROUND ART

A technical innovation associated with regenerative therapy, in particular a method for preparing pluripotent stem cells, and a method for inducing differentiation of the pluripotent stem cells, have been developed, so that studies targeting the regeneration of tissues of organisms have been intensively carried out. Also as to the heart which is indispensable for life maintenance of individual organisms, it is considered that a regenerative medical technology is utilized in the treatment of heart diseases. For example, myocardial cells artificially generated from pluripotent stem cells have been tried to be applied to the treatment of heart diseases. At this time, the myocardial cells are not used alone, but, for example, a method for forming a sheet-like cell construct containing myocardial cells has been developed (Patent Publication 1), and the usefulness of the myocardial sheet thus obtained has been shown in a model animal with myocardial infarction.

In Patent Publication 1, a myocardial sheet is produced by combining myocardial cells with endothelial cells, mural cells and Flk/KDR-positive cells and culturing the cells. Although the above publication discloses a method for preparing plural cells such as myocardial cells, endothelial cells and mural cells as a cell mixture, it is desired to individually prepare these cells, from the viewpoint of control of the quality or the production process of a myocardial sheet. In addition, it has been expected that endothelial cells are used as a material for blood vessels formed in tissues when tissues or organs other than blood vessels are artificially constructed.

Several methods have been already known for the production of endothelial cells. A method for efficiently producing endothelial cells from pluripotent stem cells is, for example, a method described in Patent Publication 2. Although the method is a method of stepwisely culturing pluripotent stem cells in plural media containing different active ingredients, there are still rooms for improvements in the quality of cells obtained.

PRIOR ART REFERENCES

Patent Publications

Patent Publication 1: WO 2012/133945
Patent Publication 2: WO 2014/192925

SUMMARY OF THE INVENTION

Problems to be Solved by the Invention

In order to use endothelial cells as a material for producing a myocardial sheet as mentioned above and to use endothelial cells themselves as a medical composition or a material for a research, a method for efficiently producing endothelial cells with higher quality is desired. The term "endothelial cells with high quality" as used herein refers to endothelial cells having one or more characteristics such as the cell numbers obtained are high, the purity is high (high positive ratio of endothelial cell markers), the differentiation stage is homogenous, having excellent cell proliferation ability (for example, juvenile), being less susceptible to damage by freezing and thawing, and having small differences between lots.

The present invention intends to solve the problems owned by the conventional production methods, and an object of the present invention is to provide a method for producing endothelial cells with high quality.

Means to Solve the Problems

As the result of intensive studies to solve problems mentioned above, the present inventors have found for the first time that when the endothelial cells are induced from pluripotent stem cells, a large amount of high-purity endothelial cells can be obtained by culturing endothelial progenitor cells in the presence of a medium containing RepSox. Further, the present inventors have revealed that most of the endothelial cells obtained by the above method are juvenile endothelia cells and keep high viability and proliferation rate even after cryopreservation. The present invention has been completed on the basis of the above findings.

Concretely, the present invention relates to:
[1] a method for producing endothelial cells, including carrying out:
(a) inducing a population of mesoderm-lineage cells containing endothelial progenitor cells from pluripotent stem cells without forming an embryoid body; and
(b) culturing the population of mesoderm-lineage cells containing endothelial progenitor cells in the presence of RepSox, in this order.
[2] the method according to the above [1], wherein the pluripotent stem cell is an embryonic stem cell (ES cell) or an induced pluripotent stem cell (iPS cell);
[3] the method according to the above [1] or [2], wherein in the step (a) the pluripotent stem cell is sequentially cultured in
(i) a medium containing activin A,
(ii) a medium containing bone morphogenetic protein 4, and
(iii) a medium containing vascular endothelial growth factor;
[4] the method according to the above [3], wherein (ii) the medium containing bone morphogenetic protein 4 further contains basic fibroblast growth factor;
[5] the method according to any one of the above [1] to [4], characterized by further including, subsequent to the step (a), (a') isolating endothelial progenitor cells from the population of mesoderm-lineage cells;
[6] the method according to the above [5], wherein in the step (a') kinase insert domain receptor-positive cells are isolated as endothelial progenitor cells;
[7] the method according to any one of the above [1] to [6], wherein, prior to the step (b), the population of mesoderm-lineage cells containing endothelial progenitor cells or the isolated endothelial progenitor cells are cultured in a medium without RepSox;
[8] the method according to any one of the above [1] to [7], characterized by further including, subsequent to the step (b), (c) freezing endothelial cells;
[9] a method for producing a myocardial sheet, including: producing endothelial cells according to a method as defined in any one of the above [1] to [8], and
mixing the endothelial cells with myocardial cells and mural cells to culture the cells; and

[10] a cell composition containing kinase insert domain receptor-positive endothelial progenitor cells and RepSox.

Effects of the Invention

According to the method of the present invention, endothelial cells with high quality can be efficiently produced from pluripotent stem cells. The endothelial cells obtained according to the method of the present invention are useful in the production of, for example, a myocardial sheet, and expected to be used for the treatment of a heart disease. Further, the cells can be used as a cell model of diseases caused by abnormality or the like of endothelial cells, or as a material of safety evaluation for drugs. In addition, a myocardial sheet can be produced by mixing the endothelial cells obtained by the method of the present invention with myocardial cells and mural cells, and culturing the cells.

MODES FOR CARRYING OUT THE INVENTION

The present invention will be explained in detail hereinbelow.

The term "pluripotent stem cell" as used herein refers to a stem cell having pluripotency capable of differentiating into plural kinds of cells, and also having self-proliferation ability, and the pluripotent stem cell includes, for example, but not limited to, an induced pluripotent stem cell (iPS cell), an embryonic stem cell (ES cell), a germline stem cell (GS cell), an embryonic germ cell (EG cell), an embryonic stem cell derived from cloned embryo obtained by nuclear transfer (nuclear transfer ES cell; ntES cell), a fused stem cell, and the like. A preferred pluripotent stem cell is an iPS cell or an ES cell, and a more preferred pluripotent stem cell is an iPS cell.

The iPS cell is a somatic-cell-derived artificial stem cell, which has almost the same properties as an ES cell, for example, differentiation pluripotency and proliferation ability by self-replication, and the iPS cell can be produced by introducing specific nuclear reprogramming substances in the form of nucleic acids or proteins into a somatic cell or by increasing expression levels of endogenous mRNAs and/or proteins of the nuclear reprogramming substances with agent(s) (K. Takahashi and S. Yamanaka (2006), *Cell*, 126: 663-676; K. Takahashi et al. (2007), *Cell*, 131: 861-872; J. Yu et al. (2007), *Science*, 318: 1917-1920; and M. Nakagawa et al. (2008), *Nat. Biotechnol.*, 26: 101-106). The nuclear reprogramming substance may be a gene specifically expressed in an ES cell, or a gene or a gene product thereof playing an important role in maintenance of undifferentiated state of an ES cell. The substance includes, for example, but not particularly limited to, Oct3/4, Klf4, Klf1, Klf2, Klf5, Sox2, Sox1, Sox3, Sox15, Sox17, Sox18, c-Myc, L-Myc, N-Myc, TERT, SV40 large T antigen, HPV16 E6, HPV16 E7, Bmil, Lin28, Lin28b, Nanog, Esrrb or Esrrg. These nuclear reprogramming substances may be used in combination when establishing iPS cell. For example, the combination includes at least one, two or three, and preferably the combination includes four of the above nuclear reprogramming substances.

Human iPS cell line established as a cell line may be used in the embodiment of the present invention. A preferred human iPS cell line is, but not particularly limited to, ChiPSC7, ChiPSC11, ChiPSC12, ChiPSC19, ChiPSC20, ChiPSC21, ChiPSC22, ChiPSC23, 201B7, 201B7-Ff, 253G1, 253G4, 1201C1, 1205D1,1210B2 and 836B3, and a more preferred human iPS cell line is ChiPSC12. The above mentioned human iPS cell lines are available from Cellartis, or iPS Academia Japan, Inc., or Center for iPS Cell Research and Application, Kyoto University.

The ES cell is a stem cell which has been established from inner cell mass of early embryo (for example, blastocyst) of a mammal such as human or mice, and has differentiation pluripotency and proliferation ability by self-replication. The ES cell has been discovered in mice in 1981 (M. J. Evans and M. H. Kaufman (1981), *Nature* 292: 154-156), and subsequently, the ES cell has been established also in primates such as human and monkey.

The ES cell can be established by extracting an inner cell mass from a blastocyst of a fertilized egg of a subject animal and culturing the inner cell mass on a feeder of fibroblasts. In addition, the maintenance of cells by subculturing can be carried out by using a medium supplemented with a substance such as LIF or bFGF. The method for establishment and maintenance of ES cell of human and monkey is described in, for example, H. Suemori et al. (2006), *Biochem. Biophys. Res. Commun.*, 345: 926-932; H. Kawasaki et al. (2002), *Proc. Natl. Acad. Sci. USA*, 99: 1580-1585, and the like. In addition, some research organizations distribute ES cells. For example, KhES-1, KhES-2 and KhES-3 which are human ES cell lines are available from Institute for Frontier Medical Science, Kyoto University (Kyoto, Japan).

The culturing of pluripotent stem cells is carried out by preferably subjecting pluripotent stem cells prepared according to any methods to an adhesion culture in an appropriate culture vessel/culture substrate. Here, the adhesion culture refers to the culturing of cells in a state in which cells are adhered to a culture vessel/culture substrate. In the adhesion culture, an embryoid body (EB) is not formed. The adhesion culture is carried out by using a culture vessel/culture substrate coated with a substance to which cells can be adhered. The substance to which cells can be adhered includes, for example, various extracellular matrices (collagen, gelatin, laminin, fibronectin, vitronectin, entactin, heparan sulfate proteoglycan, and the like), an altered product or modified product thereof, polylysine, and a combination thereof. Preferably, Matrigel(registered trademark) or Synthemax(registered trademark), each of which is a composition containing plural extracellular matrices, is used in the present invention.

As to the culture vessel/culture substrate used in this step and other culturing steps in the present invention, those having any kinds of materials or shapes can be used so long as they do not inhibit maintenance, viability, differentiation, maturation or self-replication of the cells. The shape of the culture vessels/culture substrates is also not limited, and those having any shapes such as a flask, a plate, a dish, a bag and an incubator can be used. Various commercially available culture vessels/culture substrates may be used. Further, the culturing utilizing a culture vessel provided with a hollow thread, or a culture substrate such as beads, may be carried out.

As a basal medium, a medium usable in the culturing of animal cells can be used. For example, RPMI 1640 medium, DEF-CS medium, Medium 199, MCDB131 medium, IMDM, EMEM, αMEM, DMEM, Ham's F12 medium, Fischer's medium, mixed media thereof or the like are used as a basal medium. Further, a Xeno-free medium or a synthetic medium (Chemically-Defined medium) is also used. A commercially available medium sold as a medium for culturing pluripotent stem cells, for example, StemFit (registered trademark), mTeSR1, Essential8(trademark) or the like may be used. Preferably, DEF-CS medium is used as a basal medium. A medium may be added with serum, or may be serum-free. Optionally, for example, albumin, transferrin, growth factors, KSR, N2 supplement, B27 supplement, fatty acids, insulin, collagen precursor, lipids, amino acids, vitamins, 2-mercaptoethanol, 3'-thiolglycerol, trace elements, antibiotics, antioxidants, buffers, inorganic salts, or the like may be added thereto.

Cells at a density of, for example, from 0.5 to $20 \times 10^4$ cells/cm$^2$, preferably from 1 to $10 \times 10^4$ cells/cm$^2$ are seeded to a culture vessel coated with a substance to which cells can be adhered, and the cells are cultured in a suitable medium. The culturing period includes, for example, 12 hours or more, preferably 24 hours or more, and more preferably three days or more, but it is to be expected that an appropriate culturing period is determined depending upon the cells. In addition, a medium exchange or subculturing may be appropriately carried out during the culturing period.

A method for separating pluripotent stem cells that have been subjected to adhesion culture and other cells in the present invention from a culture vessel includes a physical method, a method using a chelator, an enzymatic method using a separating solution having a protease activity and/or a collagenase activity, for example, TrypLE(trademark) Select, Accutase(registered trademark), Accumax(registered trademark), or the like, and a combination thereof. Preferably, after dissociating colonies of pluripotent stem cells by an enzymatic method, a method for physically subjecting cells to fine dispersion is carried out. Generally, the pluripotent stem cells which have been cultured to 80% confluent against the culture vessel used are subjected to a separating operation.

(1) Method for Producing Endothelial Cells of the Present Invention (a) Step of Inducing Population of Mesoderm-Lineage Cells Containing Endothelial Progenitor Cells from Pluripotent Stem Cells Without Forming Embryoid Body This step is a step of inducing differentiation from pluripotent stem cells to a population of mesoderm-lineage cells containing endothelial progenitor cells. A population of mesoderm-lineage cells containing endothelial progenitor cells are induced from an iPS cell or an ES cell in a preferred embodiment of the present invention, and from an iPS cell in a particularly preferred embodiment. In this step, the above cell population can be induced without forming an embryoid body by preferably carrying out contact culture.

The term "population of mesoderm-lineage cells" as used herein means a cell population containing mesodermal cells themselves and/or cells generated by differentiation from mesodermal cells. The cells generated by differentiation from mesodermal cells include hemangioblasts, mesenchymal stem cells, hematopoietic stem cells, endothelial progenitor cells, cardiac progenitor cells, and the like.

The term "endothelial progenitor cells" as used herein means cells whose differentiation is directed to endothelial cells. The endothelial progenitor cells can be confirmed by analyzing expression patterns of transcriptional factors or cell-surface antigens. For example, expression patterns of transcriptional factors or cell-surface antigens, alone or in a combination, are measured, in which their expression levels are not detected or low even if detected before induction of differentiation, and are remarkably increased after the induction of differentiation. Markers effective for confirming endothelial progenitor cells include, for example, kinase insert domain receptor (KDR), FOXF1, BMP4, MOX1, SDF1 and the like. Preferably, the endothelial cell progenitor cells are cells expressing KDR. KDR is a molecule which is also referred to as vascular endothelial growth factor receptor-2: VEGFR-2 or Flk-1 as another name, and plays an important role in a process of vascularization.

This step (the step of inducing a population of mesoderm-lineage cells containing endothelial progenitor cells from pluripotent stem cells without forming an embryoid body) is not particularly limited, and an appropriate method may be selected from known methods. A preferred method for the present invention includes a method including culturing pluripotent stem cells in the presence of activin A and/or bone morphogenetic protein 4 (BMP4), to provide mesodermal cells. More preferably, a method to induce mesodermal cells from pluripotent stem cells by sequentially carrying out three-step culturing of "(i) culturing in a medium containing activin A," "(ii) culturing in a medium containing BMP4," and "(iii) culturing in a medium containing vascular endothelial growth factor (VEGF)" is exemplified. This three-step culturing will be hereinafter explained in detail.

(i) Culturing in Medium Containing Activin A

As one embodiment of the present invention, mesodermal cells can be efficiently induced by culturing pluripotent stem cells in a sandwich method with an extracellular matrix, prior to culturing the cells in a medium containing activin A. Matrigel can be used as an extracellular matrix. Concretely, pluripotent stem cells are seeded at a density of, for example, from 1 to $20 \times 10^4$ cells/cm$^2$, and preferably from 2 to $15 \times 10^4$ cells/cm$^2$ to a culture vessel coated with Matrigel, and the cells are subjected to adhesion culture in, for example, DEF-CS medium for 2 to 3 days. Thereafter, the medium is exchanged with a medium added with Matrigel which is diluted to, for example, from 1:10 to 1:300, preferably from 1:20 to 1:150, and more preferably from 1:40 to 1:80, and the cells are further cultured for 16 to 24 hours in which the entire pluripotent stem cells are coated with Matrigel. The medium of the Matrigel-coated pluripotent stem cells thus obtained is exchanged with a medium containing activin A.

The concentration of activin A added to a medium is, for example, from 10 to 1,000 ng/mL, preferably from 25 to 500 ng/mL, and more preferably 50 to 200 ng/mL. In addition, other growth factors and the like may be added to the medium within the range so as not to impair the effects of the present invention, and this addition is carried out preferably in the absence of BMP4 and VEGF.

As a basal medium, a medium usable in the culturing of animal cells can be used. For example, RPMI 1640 medium, DEF-CS medium, Medium199, MCDB131 medium, IMDM, EMEM, αMEM, DMEM, Ham's F12 medium, Fischer's medium, mixed media thereof and the like are used as a basal medium. A commercially available medium sold as a medium for culturing pluripotent stem cells may be used. Preferably, RPMI 1640 medium is used as a basal medium. A medium may be added with serum, or may be serum-free. Optionally, for example, albumin, transferrin, growth factors, KSR, N2 supplement, B27 supplement, fatty acids, insulin, collagen precursor, lipids, amino acids, vitamins, 2-mercaptoethanol, 3'-thiolglycerol, trace elements, antibiotics, antioxidants, buffers, inorganic salts or the like may be added thereto.

A preferred medium includes RPMI 1640 medium added with L-glutamine, B27 supplement and activin A. Here, L-alanyl L-glutamine dipeptide or GlutaMAX(trademark) can be added in place of L-glutamine added to the above medium or another medium in the present invention. The GlutaMAX(trademark) contains L-alanyl L-glutamine dipeptide. Since L-alanyl L-glutamine dipeptide having a stable structure does not decompose in the same manner as L-glutamine during the storage or culturing to form toxic ammonia, the L-alanyl L-glutamine dipeptide is suitable for cell culturing.

The pluripotent stem cells are subjected to adhesion culture in the medium mentioned above. The culturing temperature is, for example, but not limited to, from 30° to 40° C., and preferably 37° C. The culturing is carried out under an atmosphere of a $CO_2$-containing air, and the $CO_2$ concentration is preferably from 2 to 8%. The culturing time is, for example, from 6 hours to 5 days, and preferably from 12 to 48 hours.

(ii) Culturing in Medium Containing BMP4

The pluripotent stem cells which have been cultured in a medium containing activin A are subsequently subjected to culturing in a medium containing BMP4. This culturing may be carried out in the same manner as the culturing of the above (i), or may be carried out in a different manner from the above culturing. Preferably, the adhesion culture with an extracellular matrix, for example, the adhesion culture using Matrigel is carried out. In a case where the culturing is carried out by the same method as the above culturing, a medium may be exchanged, and the culturing may then be continued in the same vessel.

The concentration of BMP4 added to the medium is, for example, from 0.5 to 200 ng/mL, preferably from 1 to 100 ng/mL, and more preferably from 2 to 50 ng/mL.

In a preferred embodiment of the present invention, basic fibroblast growth factor (bFGF) is further added to the medium. The concentration of bFGF added to the medium usable in this embodiment is, for example, from 0.5 to 200 ng/mL, preferably from 1 to 100 ng/mL, and more preferably from 2 to 50 ng/mL. Further, other growth factors and the like may be added to the medium within the range so as not to impair the effects exhibited by the present invention, and this addition is carried out preferably in the absence of activin A and VEGF.

The medium used in this culturing can be prepared by appropriately combining the same basal medium as those mentioned above and various components. A preferred medium includes RPMI 1640 medium added with L-glutamine, B27 supplement, bFGF and BMP4.

The culturing temperature is, for example, but not limited to, from 30° to 40° C., and preferably 37° C. The culturing is carried out under an atmosphere of a $CO_2$-containing air, and the $CO_2$ concentration is preferably from 2 to 8%. The culturing time is, for example, from 12 hours to 5 days, and preferably from 2 to 4 days.

(iii) Culturing in Medium Containing VEGF

Subsequent to the culturing of the above (ii), cells are subjected to culturing in a medium containing VEGF. This culturing may also be carried out in the same manner as the culturing of the above (i) and (ii). Preferably, the adhesion culture with an extracellular matrix is carried out.

The concentration of VEGF in the medium usable in this culturing is, for example, from 10 to 2,000 ng/mL, and preferably from 50 to 500 ng/mL. Further, other growth factors and the like may be added to the medium within the range so as not to impair the effects exhibited by the present invention, and this culturing is carried out preferably in the absence of activin A and BMP4.

The medium used in this culturing can also be prepared by appropriately combining the same basal medium as those mentioned above and various components. A preferred medium includes RPMI 1640 medium added with L-glutamine, B27 supplement and VEGF.

The culturing temperature is, for example, but not limited to, from 30° to 40° C., and preferably 37° C. The culturing is carried out under an atmosphere of a $CO_2$-containing air, and the $CO_2$ concentration is preferably from 2 to 8%. The culturing time is, for example, from 6 hours to 5 days, and preferably from 12 to 48 hours.

By this culturing, the population of mesoderm-lineage cells containing endothelial progenitor cells are obtained. Here, the ratio of endothelial progenitor cells (KDR positive ratio) is, for example, 40% or more, preferably 50% or more, and more preferably 60% or more of total cell numbers.

(a') Step of Isolating Endothelial Progenitor Cells from Population of Mesoderm-Lineage Cells This step is a step of isolating endothelial progenitor cells from a population of mesoderm-lineage cells containing endothelial progenitor cells obtained in the above-mentioned step. Here, it is also possible not to carry out this step when a ratio of endothelial progenitor cells (KDR positive ratio) is already sufficiently high in the population of mesoderm-lineage cells containing endothelial progenitor cells obtained in the above-mentioned step. It is preferable that this step (a') is carried out subsequent to the step (a).

The isolation of the endothelial progenitor cells in this step is carried out by selectively capturing cells expressing endothelial progenitor cell markers mentioned above with a fluorescence-activated cell sorting (FACS), a magnetic-activated cell sorting (MACS), or the like, and then collecting the captured cells. In the above-mentioned separating means, it is advantageous that an antibody specifically binding to endothelial progenitor cell markers is utilized. Therefore, for example, an antibody or a fragment thereof that binds to KDR or other markers expressed on a surface of endothelial progenitor cells is utilized in the present invention.

Concretely, a cell population containing endothelial progenitor cells are contacted with an appropriately labeled antibody which specifically binds to an endothelial progenitor cell marker, for example, an anti-KDR antibody. Thereafter, the isolation of endothelial progenitor cells is achieved by collecting the labeled cells. For example, antibody-bound cells can be isolated by subjecting a cell population contacted with an fluorescence labeled antibody to a separation by FACS. In addition, in a case where an antibody labeled with a magnetic material is used, MACS or the like can be utilized. Further, the above antibody may be combined with another antibody (secondary antibody) specifically binding to the label attached to the above antibody or the antibody itself. In this case, the separation of cells is carried out by using a label attached to the secondary antibody. A commercially available antibody can be used as the above anti-KDR antibody or the secondary antibody. For example, "anti-KDR antibody bonded with a PE fluorescent label" and "magnetic beads embedding anti-PE antibodies" can be used, without being particularly limited thereto.

The ratio of the isolated endothelial progenitor cells (KDR positive ratio) is, for example, 70% or more, preferably 80% or more, and more preferably 90% or more.

The isolated endothelial progenitor cells can be directly differentiated to endothelial cells, or the endothelial progenitor cells can be differentiated to endothelial cells after maintenance culturing one time, while keeping the differentiation state of the endothelial progenitor cells.

In a case where the endothelial progenitor cells are subjected to maintenance culturing, while keeping the differentiation state of the endothelial progenitor cells, the maintenance culturing may be carried out in the same manner as the culturing in the above-mentioned step. Concretely, the maintenance culturing is carried out by the adhesion culture using an extracellular matrix such as Matrigel. The medium used in this maintenance culturing can also be prepared by appropriately combining the same basal medium as those mentioned above with various components. A commercially available medium sold as a medium for culturing endothelial cells, for example, a medium for proliferating endothelial cells or the like may be used. A preferred medium includes RPMI 1640 medium added with L-glutamine, B27 supplement and VEGF. The medium may further contain antibiotic such as penicillin or streptomycin, or ROCK inhibitor. The ROCK inhibitor is not particularly limited so long as the inhibitor can inhibit the function of Rho kinase (ROCK), and the inhibitor includes, for example, Y-27632. The concentration of Y-27632 is, for example, from 1 to 500 µM, preferably from 3 to 200 µM, and more preferably from 10 to 50 µM. Further, other growth factors and the like may be added to the medium within the range so as not to impair the effects exhibited by the present invention, and this maintenance culturing is carried out preferably in the absence of RepSox mentioned below in detail.

The culturing time of the maintenance culturing includes, for example, 24 hours or more, preferably 2 days or more, and more preferably 3 days or more, and it is to be expected that an appropriate culturing time is determined depending upon the state of cells or culturing conditions. In addition, a medium exchange or subculturing may be appropriately carried out during the culturing period.

Usually, the number of endothelial progenitor cells does not show a remarkable increase or decrease in this step of maintenance culturing. In addition, the ratio of endothelial progenitor cells (KDR positive ratio) is hardly decreased by the maintenance culturing. For example, after the maintenance culturing is carried out for three days, the ratio of the endothelial progenitor cells (KDR positive ratio) is 70% or more, preferably 80% or more, and more preferably 90% or more.

(b) Step of Culturing Population of Mesoderm-Lineage Cells Containing Endothelial Progenitor Cells in the Presence of RepSox This step is a step of culturing the population of mesoderm-lineage cells containing endothelial progenitor cells obtained in the step mentioned above in the presence of RepSox. In a case where the step (a') is carried out, the endothelial progenitor cells are cultured in the presence of RepSox in this step.

The population of mesoderm-lineage cells containing endothelial progenitor cells or endothelial progenitor cells obtained in the step mentioned above are subsequently subjected to culturing in a medium containing RepSox. This culturing step may be carried out in the same manner as the culturing in the step mentioned above, or may be carried out in a different manner from the culturing in the step mentioned above. Preferably, the adhesion culture with an extracellular matrix is carried out. In a case where the culturing is carried out in the same manner as the culturing in the step mentioned above, a medium is exchanged, and the culturing may then be continued in the same vessel. In a case where a culture vessel coated with Matrigel is used, for example, a population of mesoderm-lineage cells containing endothelial progenitor cells or endothelial progenitor cells are seeded at a density of from 0.5 to $10 \times 10^4$ cell/cm$^2$, and preferably from 1 to $5 \times 10^4$ cell/cm$^2$, and the cells are cultured in a medium containing RepSox. Since endothelial progenitor cells are differentiated into endothelial cells for the first time by using RepSox in this step, it is preferable that the population of mesoderm-lineage cells containing endothelial progenitor cells or isolated endothelial progenitor cells are cultured in a medium without containing RepSox, prior to this step (b).

RepSox (CAS No. 446859-33-2) is a low-molecular weight compound which is also referred to as E-616452, SJN2511, Alk5 Inhibitor II, TGF-βRI Kinase Inhibitor II, or the like as another name. RepSox is a strong selective inhibitor of ALK5, one of TGF-β receptors, which suppresses the function of TGF-β by inhibiting ALK5. RepSox is one of TGF-β inhibitors. Here, the transforming growth factor (TGF)-β is one of naturally occurring growth factors having many characteristics, that plays in an important role in tissue development, cell differentiation, embryonic growth, and the like.

SB431542 (CAS No. 301836-41-9) is a low-molecular weight compound that inhibits ALK4, ALK5 and ALK7, each of which is TGF-β receptor. SB431542 suppresses the function of TGF-β by inhibiting a group of receptors mentioned above. SB431542 is one of TGF-β inhibitors.

The concentration of RepSox usable in this step is not particularly limited so long as RepSox can achieve the desired effects such as inducing endothelial cells in high efficiency. The concentration of RepSox added to a medium used in this step is, for example, from 0.5 to 100 µM, preferably from 1 to 50 µM, and more preferably from 3 to 30 µM.

The medium used in this step can also be prepared by appropriately combining the same basal medium as those mentioned above with various components. A preferred medium includes a medium for proliferating for endothelial cells added with RepSox.

The culturing time in the presence of RepSox includes, for example, from 24 hours to 14 days, and preferably from 2 to 7 days, and it is to be expected that an appropriate culturing time is determined depending upon the concentration of RepSox. In addition the concentration of RepSox may be appropriately changed.

The population of mesoderm-lineage cells containing endothelial progenitor cells or endothelial progenitor cells are cultured in the presence of RepSox, whereby the proliferation of endothelial progenitor cells can be promoted, and as a result, endothelial cells expressing endothelial cell markers can be obtained in a large amount. In addition, the endothelial cells obtained in this step have one or more characteristics such as the cell numbers obtained are high, the purity is high (high positive ratio of endothelial cell markers), the differentiation stage is homologous, having excellent cell proliferation ability (for example, being juvenile), being less susceptible to damage by freezing and thawing, and having small differences between lots.

The term "endothelial cells" as used herein means cells expressing at least one of endothelial cell markers such as PE-CAM (CD31), VE-cadherin (CD144), Endoglin (CD105) and von Willebrand factor (vWF). Here, cells expressing CD31 are preferred, and cells expressing both of CD31 and CD144 are more preferred. The endothelial cells obtained by the present invention contain CD31-positive cells in a ratio of, for example, 70% or more, preferably 80% or more, and more preferably 90% or more, without particularly limiting the present invention thereto.

The endothelial cells can be more finely classified depending upon differentiation stages thereof. Among the endothelial cells, cells that are more undifferentiated are called as "juvenile endothelial cells," and cells with progressed differentiation are called as "mature endothelial cells." The differentiation stage of endothelial cells can be confirmed by analyzing expression patterns of transcriptional factors or cell-surface antigens. Concretely, the expression patterns of transcriptional factors or cell-surface antigens, alone or in a combination, are measured, in which their expression levels are remarkably changed depending upon the progress of differentiation of endothelial cells. Markers effective for confirming the differentiation stage of endothelial cells include, for example, the above-mentioned endothelial cell markers (CD31, CD144, CD105, vWF) and CD34. CD34 is a marker of hematopoietic stem cells or endothelial progenitor cells. In addition, CD34 is also expressed on the juvenile endothelial cells. The cells expressing both of CD31 and CD34 (hereinafter, CD31+/CD34+ cells) are, but not particularly limited to, one example of juvenile endothelial cells. The endothelial cells obtained by the present invention contain juvenile endothelial cells in a large amount, and, for example, the cells contain CD31+/CD34+ cells in a ratio of 70% or more, preferably 80% or more, and more preferably 90% or more, without particularly limiting the present invention thereto.

According to the method for producing endothelial cells of the present invention, various endothelial cells such as vascular endothelial cells, lymphatic endothelial cells or corneal endothelial cells can be produced.

Larger amounts of endothelial cells can be obtained by continuing the culturing of endothelial cells. As a medium used in this step, a medium prepared by appropriately combining a basal medium and various components may be used, and it is preferable that this step is carried out in the absence of RepSox. A commercially available medium sold as a medium for culturing endothelial cells, for example, a medium for proliferating endothelial cells may be used. For example, endothelial cells can be produced by using a medium for proliferating endothelial cells, and continuing the culturing while carrying out medium exchange and subculturing every 1 to 3 days. The endothelial cells thus produced can maintain the properties of endothelial cells for a long term.

In addition, a large decrease of endothelial cell markers is not observed in this step (b). The endothelial cells can maintain, but not particularly limited to, a CD31 positive ratio exceeding 60%, and preferably a CD31 positive ratio exceeding 80%, even 30 days after the beginning of the induction of differentiation.

(c) Step of Freezing Endothelial Cells

This step is a step which is carried out after step (b), and is a step of freezing endothelial cells obtained in a series of the steps mentioned above. The freezing of endothelial cells is carried out by suspending endothelial cells in a solution containing a cryoprotectant, dispensing this suspension in an appropriate storage vessel, and freezing the storage vessel according to an appropriate method.

As a cryoprotectant usable in the step of freezing endothelial cells, any of cryoprotectants can be used so long as the cryoprotectants do not inhibit the maintenance, viability, differentiation, maturation or self-replication of the cells. For example, glycerol, ethylene glycol, dimethyl sulfoxide, sucrose, glucose, polyvinyl pyrrolidone, trehalose or the like can be used. Various commercially available cryoprotectants may also be used. For example, STEM-CELLBANKER (registered trademark), manufactured by Nippon Zenyaku Kogyo Co., Ltd., and preferably CELLBANKER(registered trademark), manufactured by Nippon Zenyaku Kogyo Co., Ltd. are used as a cryoprotectant. For example, endothelial cells are, but not particularly limited to, suspended in CELLBANKER so as to have a concentration of from 0.5 to $10 \times 10^6$/mL, and preferably from 1 to $5 \times 10^6$/mL, and the suspension is dispensed to a storage vessel.

As a storage vessel, those having any materials and shapes can be used so long as the vessel does not inhibit the maintenance, viability, differentiation, maturation or self-replication of the cells. The shape of the storage vessel also is not particularly limited, and the vessel having any shapes such as vial, flask or bag can be used. Various commercially available storage vessels may be used. For example, a vial is used as a storage vessel.

As a freezing method, any methods are carried out so long as the method does not inhibit the maintenance, viability, differentiation, maturation or self-replication of the cells. For example, slow freezing is carried out, without being particularly limited thereto. Slow freezing can also be carried out with a programmed freezer, and slow freezing can also be carried out by using a frozen-treated vessel such as BICELL.

The frozen endothelial cells may be stored in a liquid nitrogen, a deep freezer held at $-80°$ C., or the like. When the cells are stored in a liquid nitrogen, the endothelial cells can be stored for, for example, 24 hours or more, preferably 3 days or more, and more preferably 2 weeks or more.

As a method for thawing the frozen endothelial cells, any of methods are carried out so long as the methods do not inhibit the maintenance, viability, differentiation, maturation or self-replication of cells. For example, the cells are warmed with a water bath warmed to $37°$ C. and thawed, without being particularly limited thereto. The viability of the thawed endothelial cells is 60% or more, preferably 70% or more, and more preferably 80% or more.

The culturing of the thawed endothelial cells may be carried out in the same manner as the culturing of other cells in the present invention. Concretely, the culturing is preferably carried out by the adhesion culture with an extracellular matrix. A medium used in this culturing can also be prepared by appropriately combining the same basal medium as those mentioned above and various components. A preferred medium includes a medium for proliferating endothelial cells. The culturing time includes, for example, 24 hours or more, preferably 3 days or more, and more preferably 7 days or more, and it is to be expected that an appropriate culturing time is determined depending upon an amount of cells required. In addition, a medium exchange or subculturing may be appropriately carried out during the culturing period. For example, in a case where the culturing is carried out for 7 days, the endothelial progenitor cells are increased to, for example, 1.1 times or more, preferably 1.3 times or more, and more preferably 1.5 times or more. In addition, a ratio of endothelial cells (CD31 positive ratio) is hardly decreased. For example, after the culturing is carried out for 7 days, the ratio of endothelial cells (CD31 positive ratio) is 80% or more, preferably 90% or more, and more preferably 95% or more.

(2) Method for Producing Myocardial Sheet of the Present Invention

The endothelial cells obtained by the present invention mentioned above can be used for production of a myocardial sheet containing endothelial cells as a constituent. For example, Japanese Patent Laid-Open No. 2012-210156 describes a method for producing a myocardial sheet in which Flk/KDR-positive cells are mixed with myocardial cells, endothelial cells and mural cells to form a sheet. A myocardial sheet can be produced in accordance with a method described in Japanese Patent Laid-Open No. 2012-210156 using the endothelial cells produced in the present invention, without particularly limiting the present invention thereto.

The term "myocardial sheet" as used herein refers to a sheet-like cell construct composed of various cells forming the heart or blood vessels, in which cells are connected with each other via intercellular binding. Here, various cells forming the heart or blood vessels include myocardial cells, endothelial cells and mural cells. A method for producing a myocardial sheet in accordance with the method described in Japanese Patent Laid-Open No. 2012-210156 will be hereinafter explained.

<Step of Producing Myocardial Cells>

This step is the step of producing myocardial cells from pluripotent stem cells, which is achieved by a known method. Myocardial cells can be obtained by, for example, culturing pluripotent stem cells in accordance with a method described in WO 2012/133954, without being particularly limited thereto.

<Step of Producing FLK-positive Cells and Mural Cells>

FLK-positive cells can be obtained by culturing pluripotent stem cells in accordance with any methods, for example, a method described in Yamashita et al. (2000), Nature, 408: 92-96. In addition, a mixture of cells of endothelial cells and mural cells can be obtained by culturing FLK-positive cells on the basis of the description of the same reference. Further, mural cells can be isolated by using an antibody specifically binding to a mural cell marker. Here, the mural cells mean cells exhibiting properties equivalent to those of blood vessel wall cells (cells surrounding vascular endothelial cells from outside thereof) or progenitor cells thereof.

<Step of Producing Myocardial Sheet>

FLK-positive cells are cultured on a temperature-sensitive culture vessel, for example UpCell, manufactured by CellSeed Inc., or the like. After the cells are cultured for 1 to 7 days, for example, after 3 days, the mixture of cells of endothelial cells and mural cells prepared by the method of the present invention, and myocardial cells are added to a culture vessel in proper amounts. This mixture of cells is cultured in a medium containing vascular endothelial growth factor (VEGF) for 1 to 10 days, for example, 4 days, thereby forming a sheet-like cell construct. A myocardial sheet thus formed can be removed from the culture vessel by allowing a culture vessel to stand at room temperature, whereby the myocardial sheet can be collected. Further, the produced myocardial sheet is laminated, as desired.

The myocardial sheet thus produced can be used for the treatment of a heart disease, for example, heart failure, myocardial infarction, ischemic heart disease, myocarditis, various cardiomyopathy, or other applications. For example, as to a heart disease such as myocardial infarction, a myocardial sheet is placed so as to cover desired sites of the heart, thereby carrying out the treatment. A myocardial sheet is taken to a heart tissue, to promote the recovery of function of the heart.

According to the present invention, in addition to a method for producing endothelial cells and a method for producing a myocardial sheet, endothelial cells produced by the method and a myocardial sheet produced by the method are also provided.

(3) Cell Composition of the Present Invention

A cell composition of the present invention contains kinase insert domain receptor (KDR)-positive endothelial progenitor cells and RepSox, and the composition is used in the production of endothelial cells in vitro.

The KDR-positive endothelial progenitor cells contained in the cell composition of the present invention can be prepared by differentiating pluripotent stem cells in accordance with a known method. For example, the endothelial progenitor cells can be obtained by using pluripotent stem cells such as ES cells or iPS cells as a material, and carrying out step (a) among the above method for producing endothelial cells of the present invention, or carrying out the step (a) and the step (b). The above step (a') may be further carried out as needed. Here, the content of the KDR-positive endothelial progenitor cells contained in the cell composition is, for example, but not particularly limited to, 70% or more, preferably 80% or more, and more preferably 90% or more, of the cells that are KDR-positive.

The concentration of RepSox contained in the above cell composition is not particularly limited so long as the desired effects such as inducing endothelial cells in high efficiency can be achieved. The concentration of RepSox is, for example, from 0.5 to 100 μM, preferably from 1 to 50 μM, and more preferably from 3 to 30 μM.

The above-mentioned cell composition can contain a medium prepared by appropriately combing the same basal medium as those used in other steps in the present invention and various components. A preferred medium includes a medium for proliferating endothelial cells added with RepSox.

The above-mentioned cell composition is cultured for, for example, from 24 hours to 14 days, and preferably from 2 to 7 days, thereby inducing the differentiation from endothelial progenitor cells into endothelial cells, whereby endothelial cells expressing endothelial cell markers can be obtained. It is to be expected that an appropriate culturing time is determined depending upon the concentration of RepSox used.

EXAMPLES

The present invention will be described more particularly by the following Examples, without intending to limit the scope of the present invention to these Examples.

Example 1 Differentiation from iPS Cells into Vascular Endothelial Cells

Human iPS cells (ChiPSC12 strain) (Cellartis) were cultured in DEF-CS medium (Cellartis) in accordance with the instructions attached to the medium.

In order to efficiently induce differentiation of mesodermal cells, iPS cells were coated with Matrigel (Matrigel Sandwich method) in accordance with the following procedures. First, TrypLE(trademark) Select (Life technologies) was added to iPS cells that had been subcultured, and the cells were incubated at 37° C. for 3 to 7 minutes. The detached cells were collected as a single cell by pipetting, and the cell numbers were counted. Next, the cells were seeded at a density of $6 \times 10^4$ cells/cm$^2$ to a culture vessel coated with Matrigel(trademark) (Corning), and cultured in DEF-CS medium for 2 to 3 days. Thereafter, the medium was exchanged with DEF-CS medium added with Matrigel diluted to 1:60, and the cells were cultured for additional 16 to 24 hours, thereby coating an upper layer of the cells with Matrigel.

The Matrigel-coated iPS cells obtained were differentiated into mesodermal cells in accordance with the following procedures. First, a medium of the Matrigel-coated iPS cells was exchanged with RPMI 1640 medium (Gibco) added with 100 ng/mL activin A (R&D), 2 mM GlutaMAX(trademark) (Thermo Fisher Scientific), and B27 supplement (without containing insulin) (Gibco) (this time point being defined as the beginning of the induction of differentiation=Day 0), and the cells were cultured for 24 hours (Day 1). Next, the medium was exchanged with RPMI 1640 medium added with 10 ng/mL human bone morphogenetic protein 4 (hBMP4) (R&D), 10 ng/mL human basic fibroblast growth factor (hbFGF) (Peprotech), 2 mM GlutaMAX, and B27 supplement, and the cells were cultured for 3 days (Day 4). Thereafter, the medium was exchanged with RPMI 1640 medium added with 100 ng/mL vascular endothelial growth factor (VEGF) (Peprotech), 2 mM GlutaMAX, and B27 supplement, and the cells were cultured overnight (Day 5). Here, as a result of observation of the cultured cells with an optical microscope, the formation of an embryoid body could not be confirmed through Day 0 to Day 5.

Kinase insert domain receptor (KDR)-positive cells were separated from the cultured cells at Day 5 with a magnetic-activated cell sorting [MACS(registered trademark), Miltenyi biotech], thereby isolating vascular endothelial progenitor cells. In order to separate the KDR-positive cells, an anti-KDR antibody (Miltenyi biotech) to which a PE fluorescent label was bound was used as a primary antibody for labeling cells, and cells labeled with the primary antibody were collected with magnetic beads (Miltenyi biotech) embedding anti-PE antibodies. When the ratio of KDR-positive cells existing in cells which were separated by MACS was measured with a flow cytometry, the KDR-positive ratio was from 89 to 99%. The cells obtained were seeded at a density of $2.7 \times 10^4$ cells/cm$^2$ to a culture vessel coated with Matrigel, and cultured in RPMI 1640 medium added with B27 supplement, 50 units/mL penicillin, 50 μg/mL streptomycin, 2 mM GlutaMAX, 20 μM Y-27632, and 100 ng/mL VEGF for 16 to 24 hours (Day 6). Further, the medium of Day 6 was exchanged with RPMI 1640 medium added with B27 supplement, 50 units/mL penicillin, 50 μg/mL streptomycin, 2 mM GlutaMAX, and 100 ng/mL VEGF, and the cells were cultured for 2 days (Day 8).

The cells were collected at Day 8, and suspended in a medium for proliferating endothelial cells (Promocell) added with RepSox at a concentration listed in Table 1. Thereafter, the cells were seeded at a density of $2 \times 10^4$ cells/cm$^2$ to a culture vessel, and cultured for 3 days (Day 11). Here, SB431542, another TGF-β inhibitor, was used as a negative control.

The cells were collected at Day 11, and the cell numbers were counted. The cells were suspended in a medium without containing a TGF-β inhibitor, i.e. a medium for proliferating endothelial cells, and seeded at a density of $2 \times 10^4$ cells/cm$^2$ to the culture vessel. The medium was exchanged every 1 to 3 days, and the cells were collected at Day 19, and the cell numbers were counted. At the same time, a part thereof was used to measure the CD31 positive cell ratio, an endothelial cell marker, with a flow cytometry. The remaining cells were suspended in a medium for proliferating endothelial cells (without containing a TGF-β inhibitor), and the cells were then seeded at a density of $1 \times 10^4$ cells/cm$^2$ to a culture vessel. The medium was exchanged every 1 to 3 days, the cells were collected at Day 30, and the cell numbers were counted. At the same time, the CD31-positive cell ratio was measured with a flow cytometry.

The cell numbers at Day 19 and Day 30 are shown in Table 1 when the cell numbers at Day 8 are defined as 1. In addition, the CD31-positive cell ratios at Day 19 and Day 30 are shown in Table 2.

TABLE 1

| TGF-β Inhibitor (Days 8 to 11) | Concentration | Cell Numbers (Day 8) | Cell Numbers (Day 19) | Cell Numbers (Day 30) |
|---|---|---|---|---|
| None | 0 μM | 1 | ND | ND |
| SB431542 (Negative Control) | 10 μM | 1 | 1.3 | 0.9 |
|  | 20 μM | 1 | 2.3 | 5.1 |
| RepSox | 3 μM | 1 | 3.1 | 2.5 |
|  | 10 μM | 1 | 3.5 | 9.1 |
|  | 20 μM | 1 | 3.5 | 3.1 |

TABLE 2

| TGF-β Inhibitor (Days 8 to 11) | Concentration | CD31-Positive (Day 19) | CD31-Positive (Day 30) |
|---|---|---|---|
| SB431542 (Negative Control) | 10 μM | 97.7% | 89.4% |
|  | 20 μM | 98.7% | 33.0% |
| RepSox | 3 μM | 98.9% | 87.0% |
|  | 10 μM | 99.7% | 99.0% |
|  | 20 μM | 99.8% | 99.1% |

It was shown that regardless of the kinds of the TGF-β inhibitors used, the CD31-positive ratios at Day 19 exceeded 97%, so that vascular endothelial cells having high purity were obtained by the method of the present invention. When SB431542 was used, the cell proliferation rate at Day 30 was 0.9 in 10 μM SB431542. In addition, while the cell proliferation rate at Day 30 was 5.1 in 20 μM SB431542, the CD31-positive ratio was 33.0%. On the other hand, when RepSox was used as a TGF-β inhibitor, the cell proliferation rates at Day 30 were 2.5 or more and CD31-positive ratios were 87% or more in both the media containing 3 μM RepSox. These results show that RepSox can satisfy both of cell proliferation rate and purity at high levels in the induction of differentiation of vascular endothelial cells, as compared to those of SB431542, and therefore, RepSox is more useful. Here, since a sufficient amount of cells was not obtained at Day 11 in a medium without adding a TGF-β inhibitor, the cells were not subcultured.

Example 2 Freezing and Thawing of Vascular Endothelial Cells

The induction of vascular endothelial cells was carried out in accordance with a method using a medium added with 20 μM RepSox described in Example 1, and the cells were collected from Days 18 to 22. The collected cells were washed, and suspended in Stem Cell Banker (TAKARA BIO INC.) so as to have a cell concentration of $3 \times 10^6$/mL, and 1 mL of each of the suspension was dispensed to vials. The vials were placed in a frozen-treated vessel (BICELL, Nihon Freezer Co., Ltd.), and the cells were subjected to slow freezing in a freezing storage chamber held at a temperature of −80° C. Thereafter, each vial was transferred to a liquid nitrogen, and stored for 3 days.

The frozen cells were warmed for 2 minutes and 30 seconds with a water bath warmed to 37° C., to thaw the cells. The cell viability was measured by using a part of the cells, and as a result, the cell viability was 87%. An entire amount of the remaining cells was added to a tube to which 8 mL of a medium for proliferating endothelial cells had been dispensed in advance. Thereafter, a vial was rinsed with 1 mL of a medium for proliferating endothelial cells, and a rinsed medium was added to the tube. The tube was centrifuged at 200×g for 5 minutes, and the supernatant was then discarded. The cells were suspended in a fresh medium for culturing endothelial cells, and the cells were seeded at a density of $2×10^4$ cells/cm² to a culture vessel. The medium was exchanged on the next day, and the medium was then exchanged every 1 to 3 days.

The cells were collected on a seventh day after thawing the cells, and the cell numbers were counted. At the same time, the CD31-positive cell ratio, an endothelial cell marker, was measured with a flow cytometry. As a result, the cell proliferation rates of from 1.5 to 4 times and the CD31 positive ratios of 95% or more (96.6 to 99%) were found. It was clarified from the results that the endothelial cells obtained by the method of the present invention had a very small damage by freezing and thawing.

Example 3 Measurement of CD31+/CD34+ Cells

Human iPS cells (ChiPSC12 strain) were cultured in DEF-CS medium in accordance with the instructions attached to the medium.

TrypLE(trademark) Select was added to iPS cells that had been subcultured, and the cells were incubated at 37° C. for 3 to 7 minutes. The detached cells were collected as a single cell by pipetting, and the cell numbers were counted. Next, the cells were seeded at a density of $6×10^4$ cells/cm² to a culture vessel coated with Matrigel(trademark), and cultured in DEF-CS medium for 2 to 3 days. Thereafter, the medium was exchanged with DEF-CS medium added with Matrigel diluted to 1:60, and the cells were cultured for additional 16 to 24 hours, thereby coating an upper layer of the cells with Matrigel.

The Matrigel-coated iPS cells obtained were differentiated into mesodermal cells in accordance with the following procedures. First, a medium of the Matrigel-coated iPS cells was exchanged with RPMI 1640 medium added with 100 ng/mL activin A, 2 mM GlutaMAX(trademark), and B27 supplement (without containing insulin) (this time point being defined as the beginning of the induction of differentiation=Day 0), and the cells were cultured for 24 hours (Day 1). Next, the medium was exchanged with RPMI 1640 medium added with 10 ng/mL hBMP4, 10 ng/mL hbFGF, 2 mM GlutaMAX, and B27 supplement, and the cells were cultured for 3 days (Day 4). Thereafter, the medium was exchanged with RPMI 1640 medium added with 100 ng/mL VEGF, 2 mM GlutaMAX, and B27 supplement, and the cells were cultured overnight (Day 5). Here, as a result of observation of the cultured cells with an optical microscope, the formation of an embryoid body could not be confirmed through Day 0 to Day 5.

KDR-positive cells were separated from the cultured cells at Day 5 by using the magnetic-activated cell sorting, thereby isolating vascular endothelial progenitor cells. In order to separate the KDR-positive cells, an anti-KDR antibody to which a PE fluorescent label was bound was used as a primary antibody for labeling cells, and cells labeled with the primary antibody were collected with magnetic beads embedding anti-PE antibodies. When the ratio of KDR-positive cells existing in the cells separated by MACS was measured with a flow cytometry, the KDR positive ratio was from 89 to 99%. The cells obtained were seeded at a density of $2.7×10^4$ cells/cm² to a culture vessel coated with Matrigel, and cultured in RPMI 1640 medium added with B27 supplement, 50 units/mL penicillin, 50 µg/mL streptomycin, 2 mM GlutaMAX, 20 µM Y-27632, and 100 ng/mL VEGF for 16 to 24 hours (Day 6). Further, the medium at Day 6 was exchanged with RPMI 1640 medium added with B27 supplement, 50 units/mL penicillin, 50 µg/mL streptomycin, 2 mM GlutaMAX, and 100 ng/mL VEGF, and the cells were cultured for 2 days (Day 8).

The cells were collected at Day 8, and suspended in a medium for proliferating endothelial cells (Promocell) added with RepSox having a concentration listed in Table 3. Thereafter, the cells were seeded at a density of $2.7×10^4$ cells/cm² to a culture vessel, and cultured for 3 days (Day 11).

The medium was exchanged with a medium without containing a TGF-β inhibitor, i.e. a medium for proliferating endothelial cells at Day 11, and the cells were collected at Day 13, and the cell numbers were counted. At this time, a part of the cells was used to measure CD31-positive cells and CD34-positive cells with a flow cytometry. The remaining cells were suspended in a medium for proliferating endothelial cells (without containing RepSox), and the cells were then seeded at a density of $2.7×10^4$ cells/cm² to the culture vessel. The medium was exchanged every 1 to 3 days, and the cells were collected at Day 13 and Day 18, and the cell numbers were counted. At the same time, CD31-positive cells and CD34-positive cells were measured with a flow cytometry.

Here, CD31 is a marker of endothelial cells, and CD34 is a marker of hematopoietic stems cells or endothelial progenitor cells. In addition, CD34 is also expressed in juvenile endothelial cells. Accordingly, CD31-positive and CD34-positive cells (hereinafter, CD31+/CD34+) in the present invention are considered to be cells of which differentiation stage has not progressed among the vascular endothelial cells, in other words, juvenile vascular endothelial cells. The CD31+/CD34+ cell ratios at Day 13 and Day 18 are shown in Table 3.

TABLE 3

| TGF-β Inhibitor (Day 8 to 11) | Concentration | CD31+/CD34+ (Day 13) | CD31+/CD34+ (Day 18) |
| --- | --- | --- | --- |
| RepSox | 3 µM | 96.9% | 93.3% |
|  | 10 µM | 96.1% | 94.4% |
|  | 20 µM | 95.8% | 96.1% |

Regardless of the concentrations of RepSox, the CD31+/CD34+ cells were 95% or more at Day 13. In addition, at Day 18, as the concentration of RepSox became higher, the proportion of CD31+/CD34+ cells became higher. These results show that juvenile endothelial cells having a potential to differentiate and mature into various endothelial cells are obtained in high proportions by using RepSox, in the induction of the differentiation of the vascular endothelial cells.

INDUSTRIAL APPLICABILITY

According to the present invention, the endothelial cells with high quality are provided. The endothelial cells of the present invention are particularly useful in the production of a myocardial sheet.

The invention claimed is:
1. A method for producing endothelial cells, comprising:
   (a) inducing a population of mesoderm-lineage cells comprising endothelial progenitor cells from human pluripotent stem cells without forming an embryoid body;
   (a') isolating the endothelial progenitor cells from the population of mesoderm-lineage cells to obtain isolated endothelial progenitor cells; and

(b) culturing the isolated endothelial progenitor cells in the presence of RepSox, wherein, in the step (a), the human pluripotent stem cells are sequentially cultured in
(i) a first medium comprising activin A,
(ii) a second medium comprising bone morphogenetic protein 4, and
(iii) a third medium comprising vascular endothelial growth factor,
wherein there is an increase in CD31-positive cells at day 19 compared to control cells.

2. The method according to claim 1, wherein the human pluripotent stem cells are human embryonic stem cells (human ES cells) or human induced pluripotent stem cells (human iPS cells).

3. The method according to claim 1, wherein the second medium further comprises basic fibroblast growth factor.

4. The method according to claim 1, wherein, in the step (a'), the isolated endothelial progenitor cells comprise kinase insert domain receptor-positive cells.

5. The method according to claim 1, wherein, prior to the step (b), the population of mesoderm-lineage cells or the isolated endothelial progenitor cells are cultured in a culture medium without containing RepSox.

6. The method according to claim 1 further comprising,
(c) freezing the isolated endothelial progenitor cells subsequent to the step (b).

7. The method according to claim 1, wherein RepSox is provided in a concentration of from 3 to 30 µM.

8. The method according to claim 1, wherein RepSox is provided in a concentration of 10-20 µM.

9. The method according to claim 1, wherein RepSox is provided in a concentration of 10 µM.

10. The method according to claim 1, wherein RepSox is provided in a concentration of 20 µM.

11. The method according to claim 2, wherein the second medium further comprises basic fibroblast growth factor.

12. The method according to claim 2, wherein, in the step (a'), the isolated endothelial progenitor cells comprise kinase insert domain receptor-positive cells.

13. The method according to claim 2, wherein, prior to the step (b), the population of mesoderm-lineage cells or the isolated endothelial progenitor cells are cultured in a culture medium without containing RepSox.

14. The method according to claim 2 further comprising,
(c) freezing the isolated endothelial progenitor cells subsequent to the step (b).

15. The method according to claim 3, wherein, in the step (a'), the isolated endothelial progenitor cells comprise kinase insert domain receptor-positive cells.

16. The method according to claim 3, wherein, prior to the step (b), the population of mesoderm-lineage cells or the isolated endothelial progenitor cells are cultured in a culture medium without containing RepSox.

17. The method according to claim 3 further comprising,
(c) freezing the isolated endothelial progenitor cells subsequent to the step (b).

18. The method according to claim 4, wherein, prior to the step (b), the population of mesoderm-lineage cells or the isolated endothelial progenitor cells are cultured in a culture medium without containing RepSox.

19. The method according to claim 4 further comprising,
(c) freezing the isolated endothelial progenitor cells subsequent to the step (b).

20. The method according to claim 5 further comprising,
(c) freezing the isolated endothelial progenitor cells subsequent to the step (b).

* * * * *

UNITED STATES PATENT AND TRADEMARK OFFICE
CERTIFICATE OF CORRECTION

PATENT NO. : 11,225,643 B2
APPLICATION NO. : 16/465920
DATED : January 18, 2022
INVENTOR(S) : Yuki Yamamoto et al.

It is certified that error appears in the above-identified patent and that said Letters Patent is hereby corrected as shown below:

On the Title Page

After the Prior Publication Data section, please insert:
-- (30) Foreign Application Priority Data
December 2, 2016 (JP)....................... 2016-234598 --

Signed and Sealed this
Seventeenth Day of May, 2022

Katherine Kelly Vidal
*Director of the United States Patent and Trademark Office*